United States Patent
Perrin et al.

(10) Patent No.: US 12,351,608 B2
(45) Date of Patent: Jul. 8, 2025

(54) METHODS OF SEPARATING PHOSVITIN AND HDL FROM AN EGG YOLK PRODUCT AND RESULTING COMPOSITIONS

(71) Applicant: Ecovatec Solutions Inc., Abbotsford (CA)

(72) Inventors: William Perrin, White Rock (CA); Christopher Nichols, Coquitlam (CA); Harry Ten Haaf, Langley (CA); Glenn Nichols, Maple Ridge (CA)

(73) Assignee: Ecovatec Solutions Inc., Abbotsford (CA)

( * ) Notice: Subject to any disclaimer, the term of this patent is extended or adjusted under 35 U.S.C. 154(b) by 915 days.

(21) Appl. No.: 17/311,664

(22) PCT Filed: Dec. 5, 2019

(86) PCT No.: PCT/CA2019/051754
§ 371 (c)(1),
(2) Date: Jun. 7, 2021

(87) PCT Pub. No.: WO2020/113341
PCT Pub. Date: Jun. 11, 2020

(65) Prior Publication Data
US 2022/0064232 A1    Mar. 3, 2022

(30) Foreign Application Priority Data

Dec. 6, 2018   (CA) ................ CA 3026673

(51) Int. Cl.
| | |
|---|---|
| *C07K 14/465* | (2006.01) |
| *A23J 1/08* | (2006.01) |
| *A23J 3/04* | (2006.01) |
| *A23J 3/34* | (2006.01) |
| *A23L 15/00* | (2016.01) |
| *A23L 33/18* | (2016.01) |
| *A61K 8/98* | (2006.01) |
| *A61K 38/00* | (2006.01) |
| *C07K 1/14* | (2006.01) |

(52) U.S. Cl.
CPC ............. *C07K 14/465* (2013.01); *A23J 1/08* (2013.01); *A23J 3/04* (2013.01); *A23J 3/341* (2013.01); *A23L 15/25* (2016.08); *A23L 33/18* (2016.08); *A61K 8/982* (2013.01); *C07K 1/14* (2013.01); *A23V 2002/00* (2013.01); *A61K 38/00* (2013.01)

(58) Field of Classification Search
None
See application file for complete search history.

(56) References Cited

U.S. PATENT DOCUMENTS 9,403,870 B2    8/2016    Wu

FOREIGN PATENT DOCUMENTS

| CA | 2838262 A1 | 12/2012 | | |
|---|---|---|---|---|
| WO | WO-2006009448 A1 | * | 1/2006 | ............ A23J 3/341 |
| WO | 2012167370 | | 12/2012 | |
| WO | WO-2012167370 A1 | * | 12/2012 | ............ A23L 15/00 |

OTHER PUBLICATIONS

Bo Jiang and Yoshinori Mine: Preparation of Novel Functional Oligophosphopeptides From Hen Egg Yolk Phosvitin; J. Agric. Food Chem. 2000, 48, p. 990-994.

Gustavo Martos et al.: In Vitro Digestions and IgE Bindings of Proteins From White and Whole Hen's Egg; Clinical and Translational Allergy 2011, 1 (Suppl 1); 08; p. 1.

Himali Samaraweera et al.: Characterisation of Phosvitin Phosphopeptides Using MALDI-TOF Mass Spectrometry; Food Chemistry, 165 (2014); p. 98-103.

Marwa Yousr and Nazlin Howell: Antioxidant and ACE Inhibitory Bioactive Peptides Purified from Egg Yolk Proteins; International Journal of Molecular Sciences 2015, 16, p. 29161-29178.

Aleksandra Zambrowicz et al.: Egg Yolk Proteins and Peptides with Biological Activity; Postepy Hig Med Dosw (online); 2014; 68: p. 1524-1529.

Mingyong Zhou et al.: Characterization of High Density Lipoprotein from Egg Yolk and its Ability to Form Nanocomplexes with Chitosan as Natural Delivery Vehicles; Food Hydrocolloids 77; 2018; p. 204-211.

S.Eftekhar, H.Parsaei, Z. Keshavarzi et al. : The Prevention and Treatment Effects of Egg Yolk High Density Lipoprotein on the Formation of Atherosclerosis Plaque in Rabbits; Iranian Journal of Basic Medical Sciences. 2015;18(4): p. 343-349.

H. Samaraweera, W. Zhang, E. J. Lee and D.U. Ahn; Egg Yolk Phosvitin and Functional Phosphopeptides; Journal of Food Science, 2011; p. 76.

S. Jung, D. U. Ahn, K.C. Nam, H. J. Kim, C. Jo; Separation of Phosvitin from Egg Yolk without Using Organic Solvents; Asian-Australasian Journal of Animal Sciences; 2013;26(11): p. 1622-1629.

G. Taborsky; Interaction Between Phosvitin and Iron and its Effect on a Rearrangement of Phosvitin Structure; Biochemistry; 1963;2; p. 266-271.

(Continued)

*Primary Examiner* — Christian L Fronda
(74) *Attorney, Agent, or Firm* — CHRISTENSEN O'CONNOR JOHNSON KINDNESS PLLC

(57) ABSTRACT

There is a method of separating phosvitin and HDL proteins from an egg yolk composition. The egg yolk composition includes HDL proteins bound to phosvitin. At least a portion of the HDL proteins are hydrolysed to cause the HDL proteins and phosvitin to become unbound and forming a hydrolysed solution comprising hydrolysed HDL, phosvitin and peptides. The hydrolysed HDL is separated from the phosvitin and peptides to form a separated hydrolysed HDL composition and a separated phosvitin and peptide solution. One resulting product is an egg yolk composition formed having at least 20% solids by mass of phosvitin phosphopeptides unbound from HDL. Another resulting product is an egg yolk composition having at least 80% hydrolysed HDL-derived lipopeptide solids by mass.

18 Claims, 4 Drawing Sheets

(56) References Cited

OTHER PUBLICATIONS

P. J. Heald and P. M. McLachlan; Isolation of phosvitin from the plasma of the laying hen; Biochem J. 1963;87:p. 571-576.

R. A. Wallace, J.P. Morgan; Isolation of phosvitin: retention of small molecular weight species and staining characteristics on electrophoretic gels; Anal Biochem. 1986;157:p. 256-261.

J. N. Losso, S.A. Nakai; A simple procedure for the isolation of phosvitin from chicken egg yolk; Egg uses a processing technologies. CAB International; Wallingford, UK: 1994. p. 150-157.

O.Castellani, V.Martinet, E. David-Briand, C. Guerin-Dubiard, M. Anton; Egg yolk phosvitin: preparation of metal-free purified protein by fast protein liquid chromatography using aqueous solvents; J Chromatogr B. 2003;791: p. 273-284.

K.Y. Ko, K. Nam, C. Jo, E. J. Lee, D.U. Ahn; A simple and efficient method for preparing partially purified phosvitin from egg yolk using ethanol and salts; Poult Sci. 2011;90: p. 1096-1104.

S.Jung, K. C. Nam, D. U Ahn, H. I Kim; Effect of phosvitin on lipid and protein oxidation in ground beef treated with high hydrostatic pressure! Meat Sci.Jo. 2013 95:p. 8-13.

B. M. Byrne, A. D. van het Schip, J. A. van de Klundert, A. C. Arnberg, and M. G. Gruber; Amino acid sequence of phosvitin derived from the nucleotide sequence of part of the chicken vitellogenin gene; Biochemistry; 1984; 23:p. 4275-4279.

International Search Report and International Search Report Written Opinion for PCT/CA2019/051754; mailed Mar. 18, 2020, 16 pages.

Jiandong Ren et al: "Preparation and Characterizaton of Phosphopeptides From Egg Yolk Phosvitin"; Journal of Functional Foods 18 (2015); p. 190-197.

Jiandong Ren: "Phosvitin Extraction and Phosphopeptides Characterization From Chicken Egg Yolk" Thesis submitted to Faculty of Graduate Studies and Research; University of Alberta; 2012; p. 1-115.

Samooel Jung et al: "Separation of Phosvitin From Egg Yolk Without Using Organic Solvents" Article in Asian Australasian Journal of Animal Sciences; Nov. 2013; p. 1-9.

Ren, J., and J. Wu, "Thermal-aided phosvitin extraction from egg yolk," Journal of the Science of Food and Agriculture 95(13):2595-2600, 2015. Abstract.

Jin, Y.-G., et al., "Effect of Phospholipase A1 on the Physicochemical and Functional Properties of Hen's Egg Yolk, Plasma and Granules," Journal of Food Biochemistry, 37:70-79, 2013.

* cited by examiner

METHODS OF SEPARATING PHOSVITIN AND HDL FROM AN EGG YOLK PRODUCT AND RESULTING COMPOSITIONS

TECHNICAL FIELD

This relates to separating phosvitin and HDL from an egg yolk product.

BACKGROUND

Phosvitin is a phosphoglycoprotein present in vertebrate egg yolks including chicken egg yolk. Phosvitin has been well documented in numerous scientific literature publications as a highly valuable protein with numerous unique functional abilities and characteristics.

Phosvitin has shown benefits as a naturally derived chelator for calcium, iron, magnesium, zinc and copper, as well as an antioxidant, antimicrobial, and emulsifier. Its peptides have shown effectiveness at increasing iron absorption, increasing bone density and calcium absorption, as an antimelanogenesis agent, a potential sepsis treatment and for its anti-cancer capabilities.

Phosvitin in chicken egg yolk is tightly bound to high-density lipoprotein (HDL) through phosphocalcic bridges. In order to extract pure phosvitin from egg yolk, one must first break or disrupt these molecular bonds.

There have been several published methods to extract phosvitin at a laboratory scale or theoretical techniques for the extraction of phosvitin at a commercial scale. The usual methodology described utilizes a salt and/or heat to break the bonds binding the phosvitin to the HDL molecule. Once the bond is disrupted, the phosvitin, soluble in the aqueous surrounding solution, becomes free floating. Then through further techniques of centrifuging and large amounts of water to dilute and then remove the salt from the solution. Other methods utilize various solvents to remove the lipids from the granule prior to utilizing salt to disrupt the HDL-phosvitin bond to free the phosvitin. Still other methods include the element of heat with salt to disrupt the bond between the HDL and the phosvitin. For example, isolating phosvitin has been performed by extracting the granules, adding a large amount of salt and heat to disrupt the phosphocalcic bridges between the HDL and phosvitin allowing the phosvitin to become free of the HDL. Centrifugation then is used to precipitate the HDL which leaves the phosvitin floating in the salt water supernatant solution. Diafiltration using ultrafiltration is then performed to desalt the solution and requires a significant amount of water to achieve low levels of salt in the finished product due to the low yield of phosvitin per kg of yolk.

There are drawbacks with these and other current methods of extracting phosvitin from egg yolk compositions.

One obstacle to development of end user products containing phosvitin or phosvitin derived phosphopeptides is the current expense associated with isolating phosvitin. Presently, there are few, if any, commercially available phosvitin products that can be produced at a cost which preserves the value of the product to the end user. A supply of commercially available phosvitin at a cost suitable for value added addition into products is needed to enable companies to start developing products containing the unique and functional phosvitin or phosvitin-derived phosphopeptides.

Additionally, delipidated protein that has been subjected to solvent and residues of some solvents potentially make them not suitable for food products. The solvents used also can denature and change the structure of the phosvitin or other proteins present, affecting their function.

SUMMARY

In one embodiment there is disclosed a method of extracting phosvitin from chicken egg yolks. The method comprises separating egg yolk granules from plasma. The granules include HDL, phosvitin and low-density lipoproteins (LDL). The method comprises introducing a hydrolysing agent into the egg yolk granules to preferentially partially hydrolyse the HDL protein bound to the phosvitin molecule and then isolating and separating the phosvitin.

In another embodiment there is a composition formed as a by-product of phosvitin extraction using the method above.

In another embodiment there is disclosed a method of extracting phosvitin from chicken egg yolk. The method comprises introducing a hydrolysing agent to hydrolyse the yolk and then centrifuging to separate the precipitate from the supernatant, the supernatant comprising unbound phosvitin, LDL, and peptides and then isolating the phosvitin.

In an embodiment there is disclosed a method separating phosvitin and HDL proteins from an egg yolk composition. The egg yolk composition includes HDL proteins bound to phosvitin. At least a portion of the HDL proteins are hydrolysed to a degree that cause the HDL proteins and phosvitin to become unbound and to form a hydrolysed solution comprising hydrolysed HDL, phosvitin and peptides. The hydrolysed HDL is separated from the phosvitin and peptides to form a separated hydrolysed HDL composition and a separated phosvitin and peptide solution.

In another embodiment there is an egg yolk composition formed from egg yolk, comprising at least 20% solids by mass of phosvitin phosphopeptides unbound from HDL.

In another embodiment there is an egg yolk composition formed from egg yolk, comprising at least 80% hydrolysed HDL-derived lipopeptide solids by mass.

The foregoing summary is not intended to summarize each potential embodiment or every aspect of the subject matter of the present disclosure.

These and other aspects of the device and method are set out in the claims.

BRIEF DESCRIPTION OF THE FIGURES

Embodiments will now be described with reference to the figures, in which like reference characters denote like elements, by way of example, and in which.

DETAILED DESCRIPTION

Figure 1:
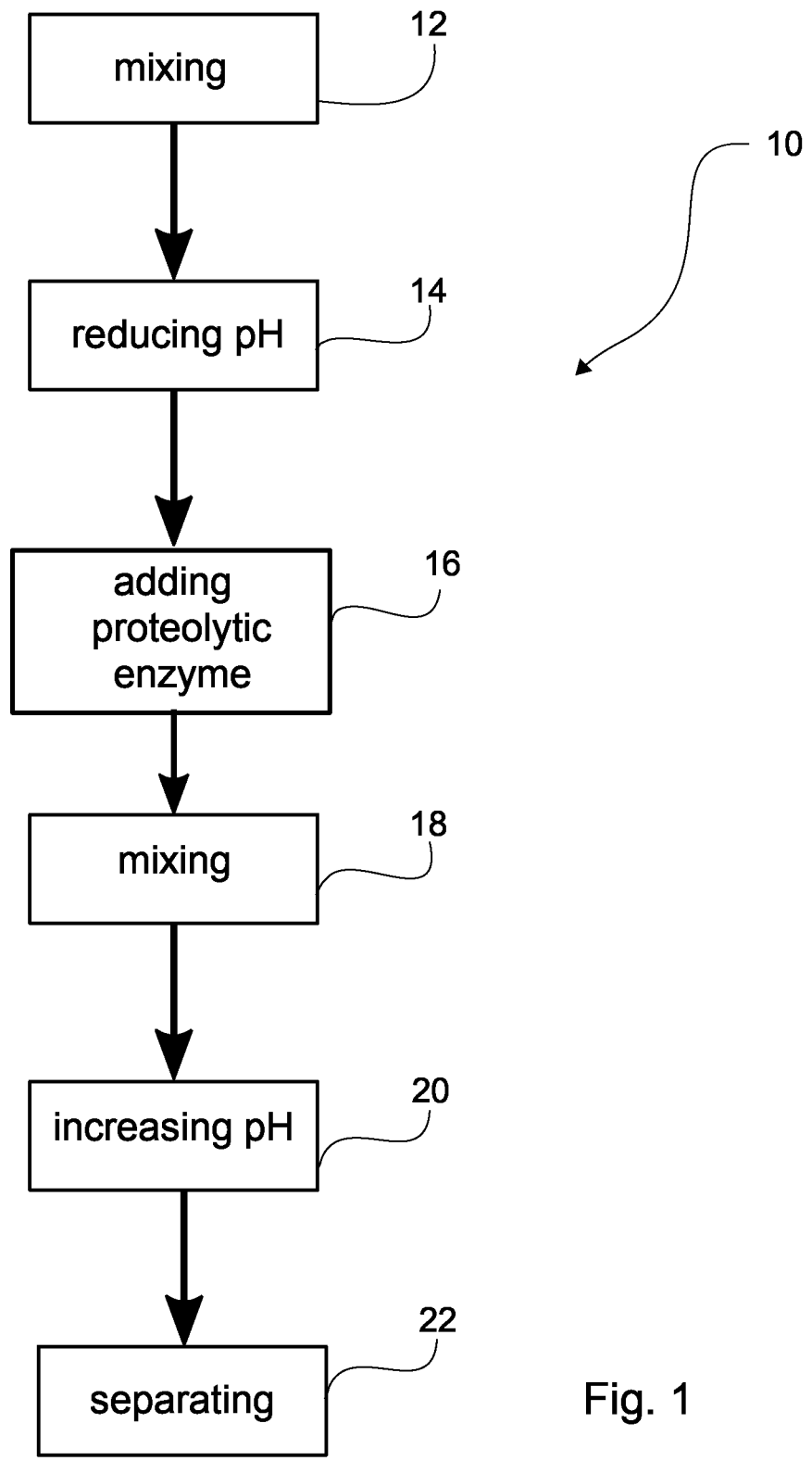
FIG. 1 is a flow diagram showing a method of separating HDL and phosvitin in an egg yolk composition.

In one embodiment there is a method of extracting significant percentages of phosvitin at a commercial scale without using solvents and without having to use large amounts of water to desalinate the separated product. Phosvitin has an amino acid composition comprised of roughly 50% serine, most of which is phosphorylated making it the most highly phosphorylated natural protein currently identified. Phosvitin's long chains of phosphorylated serine amino acids without other residues makes it highly resistant to proteolytic enzyme hydrolysis.

Phosvitin consumed on its own is described as potentially harmful due to its great ability to bind minerals. Because phosvitin is resistant to enzymatic breakdown preventing the absorption of phosvitin through the digestive tract, the phosvitin with its newly bound minerals is passed from the digestive tract, depriving the body of these essential elements. Isolation of phosvitin and subsequent breakdown of the pure protein into peptides is beneficial in order to utilize many of its properties.

Phosvitin, due to its unique, highly phosphorylated structure resists enzymatic breakdown. In one embodiment a controlled enzymatic hydrolysis acting primarily upon the underlying HDL protein structure is used, breaking down the bonds between the HDL and phosvitin, allowing the resulting unhydrolysed phosvitin to float free in the solution. This may be done without the use of high levels of salt, solvents or high heat. By not adding salt to break these bonds, this negates the need for utilizing large amounts of water to perform diafiltration to desalt the resulting solution.

Through centrifugation to remove the larger remaining hydrolysed HDL followed by selective molecular weight filtration using ultrafiltration of the supernatant a more concentrated, salt-free solution of phosvitin can be isolated. Collection of the permeate in this ultrafiltration process allows for the retention of a mixture of peptides including a percentage of phosvitin phosphopeptides also substantially free from salt allowing traditional dewatering and/or drying of the solution without special diafiltration techniques.

In a preferred embodiment, hydrolysing HDL and separating phosvitin from egg yolk granules which have been previously separated from the plasma results in three unique valuable fractions with no waste. The three fractions are: the isolated phosvitin; a unique functional egg yolk peptide product containing a portion of phosvitin phosphopeptides and peptides from HDL; and a hydrolysed HDL product with significantly reduced amounts of phosvitin bound to it. In some embodiments, there is provided a cost-effective method of obtaining phosvitin without using high amounts of salt or solvent.

Egg yolk HDL isolate has been recently shown to increase blood HDL levels in rabbits when consumed in the diet and decrease cholesterol levels in the blood and vascular walls as well as a decrease in atherosclerotic plaque size and therefore has great promise as a potential heart health treatment. It is surmised that the hydrolysed HDL isolate that is obtained herein benefits from being reduced in indigestible phosvitin which can lead to mineral deficiency while allowing it to be highly bioavailable with the potential for similar results as was shown for the HDL isolate in the study.

There is disclosed a method of separating phosvitin and high-density lipoprotein (HDL) from an egg yolk composition. The egg yolk composition includes HDL proteins bound to phosvitin. At least a portion of the HDL proteins are hydrolysed to cause the HDL proteins and phosvitin to become unbound and form a hydrolysed solution including at least hydrolysed HDL, phosvitin and peptides. The hydrolysed HDL are separated from the phosvitin and peptides to form a separated hydrolysed HDL composition and a separated phosvitin and peptide solution. The HDL may be hydrolysed by hydrolysing the HDL proteins using a proteolytic enzyme. A combination of more than one proteolytic enzymes may also be used to hydrolyse the HDL proteins and in some embodiments the more than one proteolytic enzymes may be pepsin and acid stable protease. In some embodiments, hydrolysis of the HDL proteins may be conducted until all, or substantially all, of the accessible HDL proteins are hydrolysed.

In an embodiment as shown in FIG. 1, hydrolysing the HDL proteins may be done by using a method 10 that has the following steps: mixing water with the egg yolk granules at 12, reducing the pH of the water and egg yolk granules to form a reduced pH mixture at 14, adding one or more proteolytic enzymes to the mixture at 16. In the example shown in FIG. 1, adding one or more proteolytic enzymes may include adding pepsin to the reduced pH mixture, mixing the reduced pH mixture and pepsin, adding acid stable protease to the mixture of reduced pH mixture and pepsin. The reduced pH mixture, pepsin and acid stable protease are mixed at 16. The pH of the reduced pH mixture, pepsin and acid stable protease is increased at 20 to form the hydrolysed solution.

The pepsin added may have pepsin enzyme activity as ">1:15,000" or "15,000 FCC/mg", meaning that pepsin will digest 15000 times its weight in albumen. The acid stable protease added may have an activity measurement of 4500 SAPU (Spectrophotometric Acid Protease Units), representing the amount of enzyme that will liberate one micromole of tyrosine per minute under conditions of the assay. Different activities of the proteolytic enzymes may be chosen based on parameters such as the desired length of time of the hydrolysis, or other factors such as cost.

At 22, the hydrolysed HDL are separated from the phosvitin and peptides to form a separated hydrolysed HDL composition and a separated phosvitin and peptide solution as described earlier. The steps 12 to 20 are one exemplary method of hydrolysing at least a portion of the HDL proteins to cause the HDL proteins and phosvitin to become unbound and form a hydrolysed solution including at least hydrolysed HDL, phosvitin and peptides.

The pH may be reduced by adding hydrochloric acid and may be adjusted to 2.5. The temperature may be adjusted to between 38° C. and 40° C. and maintained constant prior to the addition of pepsin. Pepsin may be added at a ratio of 1:50 per kg of protein solids in solution. The reduced pH mixture and pepsin may be mixed over a period of three hours. The acid stable protease may be added to the mixture at a ratio of 1:50 per kg of protein solids in solution. The resulting solution may be mixed for 15 hours. The temperature of that mixture may be raised to 65° C. for 5 minutes and pH is adjusted to neutral to stop the hydrolysis. The pH of the hydrolysed solution may be increased to 7.0 by adding sodium hydroxide.

The degree of hydrolysis of the HDL proteins may be controlled through, for example, selection of the enzyme or enzymes utilized, the amount of water added to the solution, the amount of each enzyme added into solution, the sequence of enzymes added if more than one, the pH of the solution throughout the hydrolysis, the temperature of the solution throughout hydrolysis and the length of time that hydrolysis occurs for each enzyme utilized. HDL proteins are present throughout the molecule with only a portion present outside of the phospholipid and accessible to aqueous enzymes. Preferably, the accessible portion of HDL proteins participating in the bonding with phosvitin are selectively hydrolysed without also hydrolysing the phosvitin.

In some embodiments, some of the accessible HDL protein will remain intact and bonded to phosvitin while some accessible HDL is hydrolysed releasing only a portion of the total available intact phosvitin. In other embodiments all or substantially all accessible HDL protein will be hydrolysed as well as a portion of the phosvitin protein but also leaving some intact and unbound phosvitin protein. In still further embodiments, both a portion of the accessible HDL will remain unhydrolysed and bound to phosvitin while another portion of HDL will be hydrolysed freeing the bound phosvitin and in either case, some portion of the separated phosvitin will be hydrolysed into peptides, while the remaining portion of separated phosvitin will be unhydrolysed and intact.

Hydrolysis can be characterised by the degree of hydrolysis which is what proportion of the available peptide bonds have been severed. A protein is made up of many amino acids joined by peptide bonds in a chain. If, for example, the protein was 101 amino acids long (100 bonds) and it has one peptide bond severed it has a degree of hydrolysis of 1%, if it has 100 of the peptide bonds severed it has a 100% degree of hydrolysis or "complete hydrolysis". In this patent document, reference to the absence of hydrolysis within a described protein, reference to selective hydrolysis "without hydrolyzing" the described protein, or reference to an unhydrolysed or intact described protein refers to a state where the peptide chain of a whole distinct protein molecule has had none of its peptide bonds broken and therefor a 0% degree of hydrolysis.

In embodiments where the HDL proteins are selectively hydrolysed without also hydrolysing the phosvitin, the objective is to use the minimal hydrolysis to hydrolyse the peptide bonds in the HDL proteins to destabilise the bonds, freeing the phosvitin while having little to no hydrolysis of the released phosvitin protein. In practice, the process will likely leave some of the phosvitin bound to the HDL while some of the phosvitin partially hydrolysed.

Hydrolysis is a concentration, pH and time dependent activity. For example, in some cases, the addition of five times the amount of enzyme can allow the hydrolysis to occur in a ⅕th of the time assuming the same ideal pH. Similarly, if pH is adjusted off of the ideal setpoint then the rate will slow down again. In order to conduct a controlled hydrolysis, without all components, such as phosvitin, being fully or partially hydrolysed, some or all of these parameters must be limited to certain ranges in order to get the desired outcome.

In another example, if time or tank space were constraints, the amount of enzyme added could be increased and the time could be reduced while still obtaining the same outcome. This example would generally be more expensive, because it would cost more in enzymes, and it might also cause some increased variability of the end product, since the hydrolysis is occurring at a faster rate so that stopping at a very specific point becomes more difficult.

Possible exemplary ranges for hydrolysing at least a portion of the HDL proteins are set out in Table 1 below:

TABLE 1

| Steps | Possible ranges | Preferred ranges and/or values |
|---|---|---|
| Water ratio (water to wet granule) | Between 100:1 and 1:1 | 3 to 1 |
| pH of hydrolysis | 1.5 to 5.5 | 2.5 |
| amount of pepsin added (pepsin to dry protein mass) | between 1:10 and 1:500 | 1 to 50 |
| temperature of pepsin hydrolysis | 10 C. to 60 C. | 38 C. to 40 C. |
| Time of pepsin only hydrolysis | 1 hour to 10 hours | 3 hours |
| amount of ASP added (ASP to dry protein mass) | between 1:10 and 1:500 | 1 to 50 |
| temperature of pepsin and ASP hydrolysis | 10 C. to 60 C. | 38 C. to 40 C. |
| Time of pepsin and ASP hydrolysis | 1 hour to 24 hours | 15 hours |
| Temperature raised after hydrolysis | optional | 65 C. |
| Time held at temperature | optional | 5 minutes |
| pH adjusted for final solution | optional | 7 |
| Filtration after hydrolysis | 50 kDa to 500 kDa | 200 kDa |
| Secondary filtration to separate phosvitin from peptides | 5 kDa to 30 kDa | 10 kDa |

The egg yolk composition preferably is in an undenatured form prior to the step of hydrolysing the HDL proteins. The original egg yolk may be egg yolk granules from an egg yolk. The egg yolk granules may be obtained by mixing water with egg yolk to form a mixed product that includes yolk plasma and granules. The yolk plasma includes proteins and phospholipids. The yolk plasma and granules are separated to form the egg yolk granules. In some embodiments, a salt may also be mixed with the water and egg yolk. The addition of salt is done to facilitate the separation of granule from the plasma and is done with less than 0.5% salt solution. However, in other embodiments, salt water need not be added to the granule so that it is not necessary to remove it later to make a suitable product.

Unbound HDL proteins may be separated from the phosvitin by diluting the hydrolysed solution with water to form a diluted hydrolysed solution and removing hydrolysed HDL from the diluted hydrolysed solution. Separation may also be achieved by centrifuging the hydrolysed solution to precipitate out the hydrolysed HDL from the supernatant phosvitin and the peptides. The separated supernatant phosvitin and peptide solution may be filtered to remove any larger intact HDL lipovitellins or LDL and lipoproteins to form a phosvitin product with a higher concentration of supernatant phosvitin and peptides. The filtering may be done using a 200 kDa filter. Using a 200 kDa filter is effective because there is a large percentage of desired phosvitin in the 35-45 kDa range and there is not any significant contaminant protein between the phosvitin band at 45 kDa and the 200 kDa level. In this filtration step some diafiltration may be performed for the purposes of yields and getting out as much of the phosvitin and YPP from that retentate solution. Only a hundred liters may be required and that amount would be dependent on the size of the UF system and there are diminishing returns on the amount of phosvitin and peptides that are flushed through to the permeate versus the amount of water that is later needed to be removed. The filtered concentration of supernatant phosvitin and peptides may be heated to at least 65° C. for approximately 10 minutes. In other embodiments, the supernatant phosvitin and peptides may be heated to at least 65° C. for at least 5 minutes. In other embodiments, the supernatant phosvitin and peptides is heated to at least 70° C. for approximately 10 minutes. In other embodiments, the supernatant phosvitin and peptides may be heated to at least 70° C. for at least 5 minutes. Filtering the separated supernatant phosvitin and peptide solution may be done using a 10 kDa filter. Secondary filtration to separate the phosvitin from the peptides could use filters in the range from 30 kDa down to 5 kDa.

The separated supernatant phosvitin and peptide solution may be dried to form a phosvitin product. A spray drier may be used to dry the solution to form a phosvitin powder. The separated hydrolysed HDL composition may be dried to form a hydrolysed HDL product. The separated hydrolysed HDL composition may be mixed into water and spray dried to form a hydrolysed HDL powder. The separated supernatant phosvitin and peptide solution may be filtered to form separately a purified phosvitin product and a purified yolk peptide product. In some embodiments, filtration may be performed using ultrafiltration of less than 20 kDa to separate the phosvitin from the smaller molecular weight peptides, for example having molecular weight of less than 20 kDa.

In some embodiments, the initial egg yolk composition is a liquid egg yolk. The initial egg yolk composition may also be a dried egg yolk.

Using the methods described herein, an egg yolk composition may be formed comprising at least 20% solids by mass of phosvitin phosphopeptides unbound from HDL. In some embodiments, the egg yolk composition may be at least 25% solids by mass of phosvitin phosphopeptides unbound from HDL. The egg yolk composition may be made into a dried powder having less than 5% moisture content.

Similarly, an egg yolk composition may be formed comprising at least 80% hydrolysed HDL-derived lipopeptide solids by mass. In some embodiments, the egg yolk composition may be formed comprising at least 90% hydrolysed HDL-derived lipopeptide solids by mass. The egg yolk composition may be made into a dried powder having less than 5% moisture content.

In various embodiments, the method does not begin with delipidated egg yolk. Not all of the proteins need to be broken down into peptides. There is a controlled hydrolysis on undenatured proteins to specifically target the HDL proteins (lipovitellins) to which the phosvitin is bound to without substantially breaking down the phosvitin. Once the attached protein is broken down, the phosvitin is then free floating and unbound in the solution.

In various embodiments, enzymes are used to selectively hydrolyse the HDL and leave the phosvitin intact through a controlled hydrolysis process. Two useful additional products are created, namely a yolk protein peptide and a hydrolysed version of HDL with a reduced phosvitin content.

After HDL proteins are hydrolysed, the resulting product is an extraction of high-density lipoproteins from the egg yolk. It has been hydrolysed to cleave the proteins into peptides within the HDL to reduce the molecular size and improve digestibility and bioavailability.

Additionally, the HDL peptides have been isolated after the removal of a significant portion of the phosvitin protein. Phosvitin, in chicken egg yolk, is bound strongly to the HDL. The phosvitin is released in large quantity from the HDL leaving the hydrolysed HDL significantly reduced in the amount of bound phosvitin protein. By reducing the bound phosvitin this may make the HDL-derived lipopeptide product more valuable as a potential supplement or nutraceutical as the negative impacts of consuming higher amounts of intact phosvitin, such as stripping minerals from the body, are significantly reduced.

Previous academic research shows the consumption of an HDL isolate from chicken egg yolk may significantly positively impact atherosclerosis in rabbits. The HDL-derived lipopeptide product which may be produced using the methods described herein, with reduced phosvitin, could be a healthy natural supplement to improve cardiovascular health within people and animals.

Figure 4:
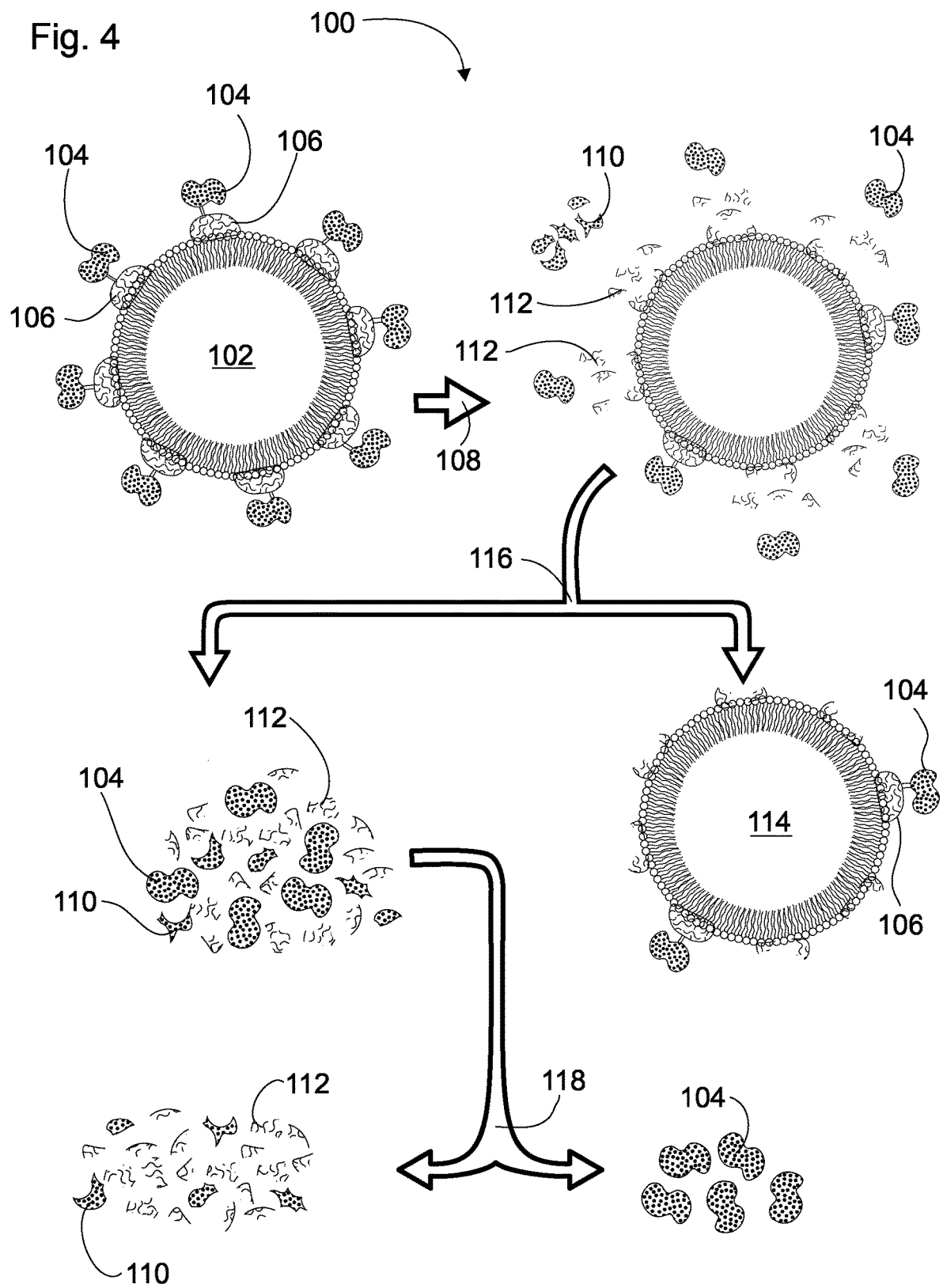
FIG. 4 is a simplified schematic of a process to remove and isolate phosvitin from egg yolk HDL and to also isolate a yolk protein peptide and an HDL-derived lipopeptide product.

In FIG. 4, shows a simplified schematic of a process 100 to remove and isolate phosvitin from egg yolk HDL as well as isolate a yolk protein peptide and an HDL-derived lipopeptide product. Initially, an egg yolk HDL 102 is bound with phosvitin 104. The phosvitin 104 is connected to HDL apoproteins 106. As shown at 108, the HDL and phosvitin are subjected to a controlled hydrolysis preferentially affecting the HDL apoproteins and disrupting the bond to phosvitin. Following the hydrolysis, the HDL apoprotein 106 is broken into protein peptides 112, and the phosvitin 104 is unbound from the HDL. In some cases, the phosvitin may itself be divided into phosvitin peptides 110. At 116, centrifugation is applied to the mixture, resulting in separation of an HDL-derived lipopeptide product 114 and a mixed phosvitin and peptide product, containing phosvitin 104, protein peptides 112 and phosvitin peptides 110. Ultrafiltration is applied to the mixed phosvitin and peptide product at 118 to form both a phosvitin product containing phosvitin 110 and a yolk protein peptide production including phosvitin peptides 114 and other protein peptides 112.

As discussed above, the methods disclosed herein may be used to produce three distinct products: isolated phosvitin, a unique functional egg yolk peptide product containing a portion of phosvitin phosphopeptides and peptides from HDL and a hydrolysed HDL product with significantly reduced amounts of phosvitin bound to it. Examples of the specific compositions of these products that may be produced are set out below.

A sample of an exemplary composition of an HDL isolate (HDLp) produced by the methods described herein was tested for certain properties in Table 2 below. The first column 'test items' represents the item that was tested. The next column 'specifications' represents the desired characteristics for the sample. The next column 'analytical values' represents the result of the test. The final column 'method' represents the type of testing method used.

TABLE 2

| Test Items | Specifications | Analytical Values | Method |
|---|---|---|---|
| Appearance/Color | Yellow-light yellow | Passed | Visual |
| Appearance/Form | Fine Powder | Passed | Visual |
| Total HDLp (protein + fat) | >85% | 91.20% | Protein + Fats |
| Protein | >40% | 44.50% | AOAC 990.03 |
| Fats | >35% | 46.70% | AOCS 954.02 |
| Moisture | <5% | 1.70% | AOAC 935.29 |
| Ash | <10% | 8.30% | AOAC 942.05, 923.03 |
| Heavy Metals*-As, Hg, Pb, Cd | NMT 10 ppm | NMT 0.2 ppm | ICPMS |
| Aerobic Plate Counts | NMT 10,000 cfu/g | 380 cfu/g | MFHPB-18 |

TABLE 2-continued

| Test Items | Specifications | Analytical Values | Method |
|---|---|---|---|
| Coliform | Not Detected | Not Detected | MFHPB-34 |
| Salmonella | Not Detected | Not Detected | MFHPB-20 |
| E. coli | Not Detected | Not Detected | MFHPB-34 |

In an embodiment, the HDL isolate is a premium HDL-derived lipopeptide (HDLp) concentrate, containing a minimum of 90% HDL-derived lipopeptides. In some embodiments, the method produces clean, high-quality egg yolk products efficiently and at lower costs than standard methods. The HDL isolate includes natural egg proteins and lipids that are not contaminated and denatured by harsh solvents as may be preferred by customers.

Hydrolysed HDL isolate may be used as a nutritional supplement ingredient. It can also be used as a healthy fat and protein source in functional foods and cosmetics. Many studies have suggested the benefits of dietary HDL and its ability to support a healthy heart and circulatory system. In some embodiments, the HDL isolate will still contain lipids and protein/peptides. The proteins in the HDL are at least partially hydrolysed and it has had a portion of the phosvitin removed from it.

A purified phosvitin product may also be produced by the methods described herein. In particular, purified phosvitin may be used for its anti-bacterial, anti-viral, anti-carcinogenic, and anti-inflammatory properties.

The purified phosvitin in this example may be a phosvitin protein product extracted naturally through the extraction techniques disclosed herein. In some embodiments, the product is a clean, high-quality egg yolk product which is produced efficiently and at lower costs than standard methods. In some embodiments, the process maintains phosvitin's full protein structure without denaturing or hydrolyzing it.

In one embodiment, a purified phosvitin product was produced by the methods described herein having the following properties as set out in Table 3 below. The first column 'test items' represents the item that was tested. The next column 'specifications' represents the desired characteristics for the sample. The next column 'analytical values' represents the result of the test. The final column 'method' represents the type of testing method used.

TABLE 3

| Test Items | Specifications | Analytical Values | Method |
|---|---|---|---|
| Appearance/Color | Off-white | Passed | Visual |
| Appearance/Form | Fine Powder | Passed | Visual |
| Solubility (Color) | Colorless to very faint yellow | Passed | Visual |
| Solubility in water (50 mg/ml to 200 mg/ml) | Clear to very slightly hazy | Passed | Visual |
| Total Protein | >75% | 85.50% | AOAC 990.03 |
| Phosphorous | > 10,000 ppm | 27,890 ppm | ICPMS |
| Moisture | <7% | 6.70% | AOAC 935.29 |
| Ash | <12% | 10.40% | AOAC 942.05, 923.03 |
| Heavy Metals*- As, Hg, Pb, Cd | NMT 10 ppm | NMT 1 ppm | ICPMS |
| Aerobic Plate Counts | NMT 10,000 cfu/g | NMT 3,900 cfu/g | MFHPB-18 |
| Coliform | Not Detected | Not Detected | MFHPB-34 |
| Salmonella | Not Detected | Not Detected | MFHPB-20 |

Figure 2:
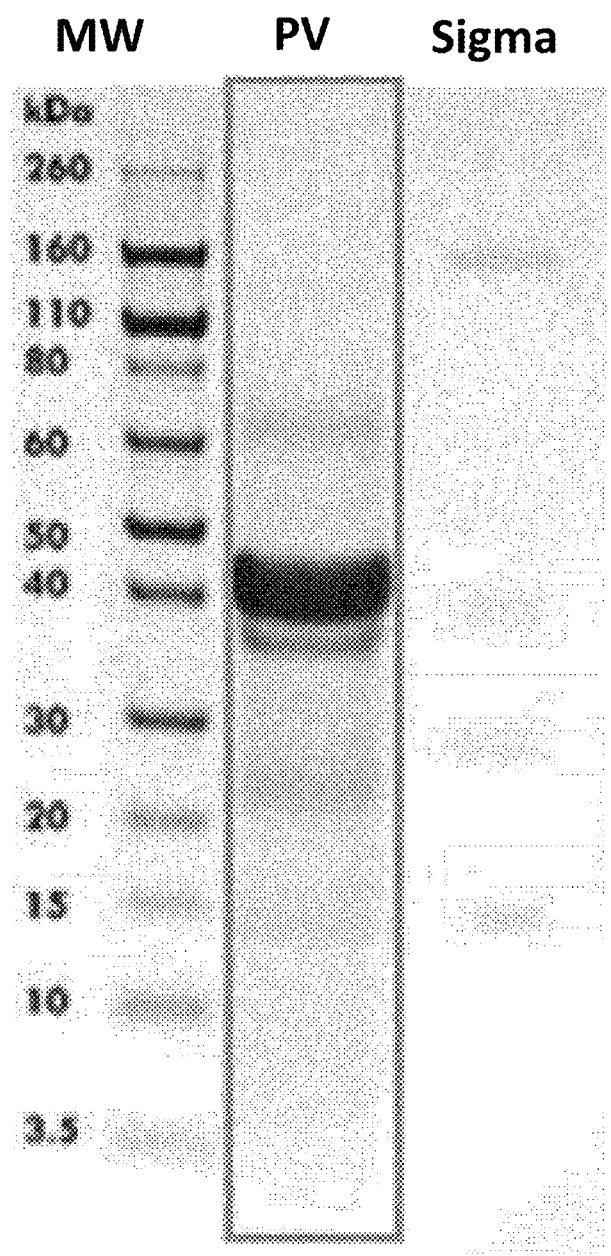
FIG. 2 is an illustration showing a gel electrophoresis profile of a purified phosvitin composition.

FIG. 2 shows a gel electrophoresis (GEP) of a purified phosvitin product made in accordance with the methods disclosed herein. The phosvitin product has 49.2% serine. Pure phosvitin protein has 50% serine. The GEP shows the purified phosvitin obtained from our process tested against a standard phosvitin obtained from Sigma Aldrich™. The MW on the left-hand column in the slide is a reference molecular weight marker run at the same time as the sample to give a reference point for the molecular weight of any band seem on the tested products. In this case, there is a very heavy band around the 40-45 kDa mark which is the molecular weight of the major fractions of phosvitin in chicken eggs and the next largest MW of phosvitin being at the 35 kDa mark. In academic literature, phosvitin has also been shown to have small percentages with bands at roughly 18 kDa, 15 kDa and 13 kDa as well as a band around 160 kDa which represents four smaller phosvitin molecules bound together.

Another product that may be produced by the methods disclosed herein is an egg yolk protein peptide product including at least 25% phosvitin phosphopeptides. The protein peptide product may be the peptides that remain after separating the phosvitin from the smaller molecular weight peptides.

The protein peptide product may be an isolate of low molecular weight peptides specifically obtained from the separated egg yolk granules (primarily HDL and phosvitin) of the egg yolk. The normal process of producing an egg yolk peptide is to take the delipidated and denatured protein from the phospholipid solvent extraction process and hydrolyse that. This would include proteins from all portions of the egg yolk not just the granule. This also has the potential of containing trace residual solvent.

In the present method, it is not necessary to denature the proteins prior to hydrolysis or have any solvents present. By first isolating the granules, it may be possible to concentrate the much higher bioactive phosvitin peptides within the peptide mix.

In some embodiments, tests have shown that the extracted protein peptide product displays many of the properties associated with the phosvitin peptides which are:

(a) High antioxidant capabilities;
(b) Mineral binding capability; and
(c) Anti-microbial capability.

The protein peptide product described in embodiments herein may be used in nutraceuticals to improve mineral absorption, as a source of easily digested protein peptides and as an antioxidant, it may also be used in cosmetics as an antioxidant, anti-bacterial agent and a source of valuable bioactive peptides.

In one embodiment, a protein peptide product was produced by the methods described herein having the following properties as set out in Table 4 below. The first column 'test items' represents the item that was tested. The next column 'specifications' represents the desired characteristics for the sample. The next column 'analytical values' represents the result of the test. The final column 'method' represents the type of testing method used.

TABLE 4

| Test Items | Specifications | Analytical Values | Method |
|---|---|---|---|
| Appearance/Color | Off white-light yellow | Passed | Visual |
| Appearance/Form | Fine Powder | Passed | Visual |
| Total Protein | >80% | 86.60% | AOAC 990.03 |

TABLE 4-continued

| Test Items | Specifications | Analytical Values | Method |
|---|---|---|---|
| Phosphorous | >3500 ppm | 3,860 ppm | ICPMS |
| Moisture | <5% | 4.50% | AOAC 935.29 |
| Ash | <10% | 7.40% | AOAC 942.05, 923.03 |
| Heavy Metals-As, Hg, Pb, Cd | NMT 10 ppm | NMT 0.3 ppm | ICPMS |
| Aerobic Plate Counts | NMT 10,000 cfu/g | NMT 5,800 cfu/g | MFHPB-18 |
| Coliform | Not Detected | Not Detected | MFHPB-34 |
| Salmonella | Not Detected | Not Detected | MFHPB-20 |
| E. Coli | Not Detected | Not Detected | MFHPB-34 |

The protein peptide product set out in Table 4 is a formulation of egg yolk protein peptides, including at least 25% phosvitin phosphopeptides. In some embodiments the phosvitin products are clean, high-quality egg yolk products efficiently and at lower costs than standard methods. The protein peptide products may be composed of natural egg proteins and lipids that are not contaminated and denatured by harsh solvents.

The protein peptide products may have a broad range of useful applications. Egg yolk protein peptides are a source of protein to enrich food products. When combined with calcium and iron supplements, the phosvitin phosphopeptides in the phosvitin products dramatically increase the absorption of calcium and iron in the intestines. In some embodiments, the phosvitin products have antioxidant, antibacterial, anti-viral, anti-carcinogenic, and anti-inflammatory properties as well as being useful as a nutraceutical additive, cosmetic ingredient, functional food, and beverage fortifier. In some embodiments, the protein peptide product is also beneficial in sports nutrition, oral care, and bone health products.

Compared to other phosvitin products, the protein peptide products, such as shown in Table 4, have a much higher portion of peptides derived from HDL and possibly phosvitin, since as an initial step, the granules are isolated which are largely made up of an HDL/phosvitin complex. The peptides produced are fairly small molecular weight and free of any other intact proteins or lipoproteins. The small molecular weight of these peptides means that they are primarily made up from amino acids chains that are only a few amino acids in length.

Figure 3:
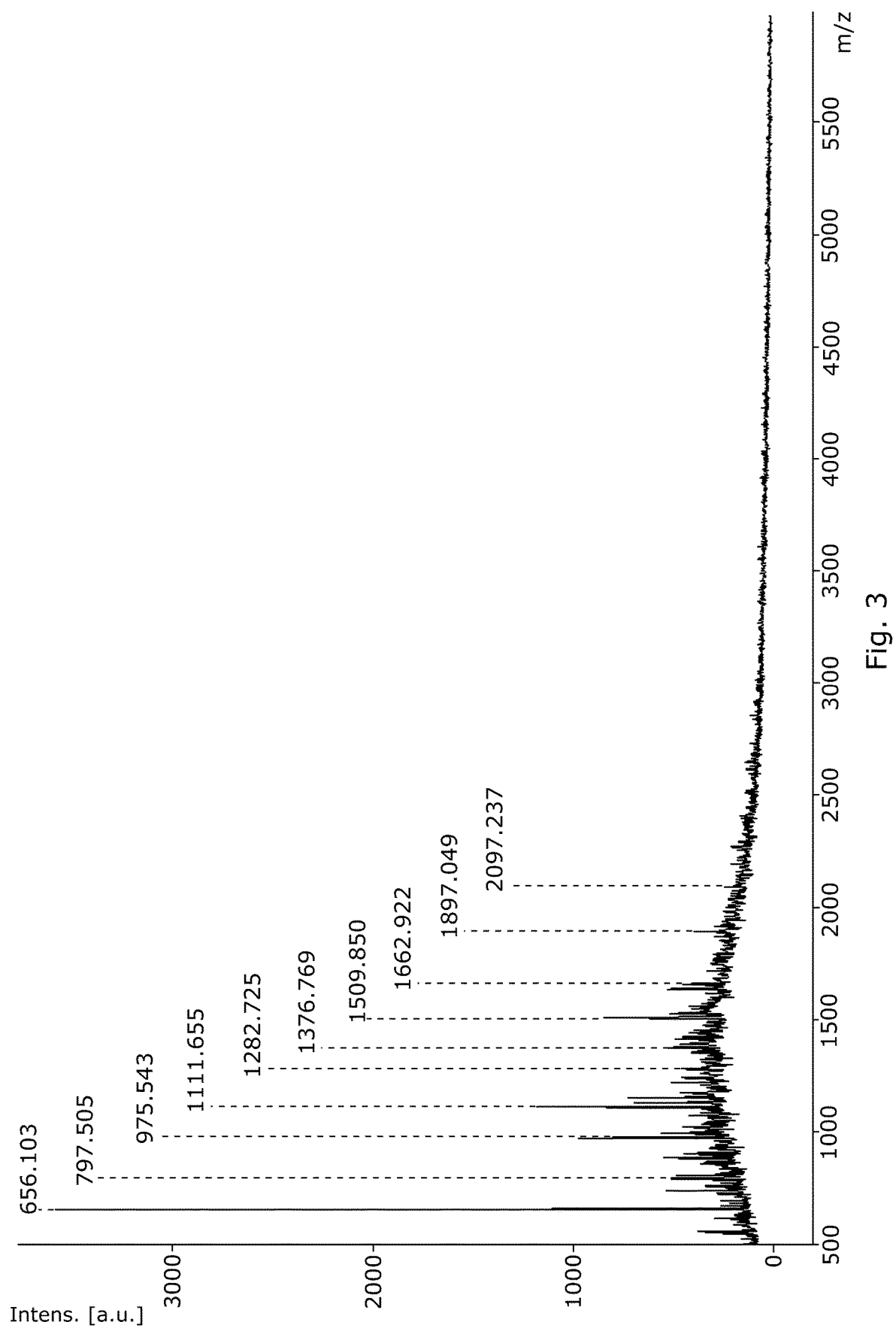
FIG. 3 is a graph showing a matrix-assisted laser desorption/ionization analysis of an egg yolk peptide product including phosvitin phosphopeptides composition.

In FIG. 3, a Matrix Assisted Laser Desorption/Ionization (MALDI) graph of the protein peptide product made in accordance with the methods disclosed herein is analyzed. The x-axis represents the molecular weight (MW) usually in m/z where z is 1, which is a ratio of mass to charge. The y-axis is the intensity with "arbitrary units" or au. The graph shows the relative magnitude of each peak relative to each other. A zero reading indicates that there are no molecules in that size present in the sample tested. The scale goes from smallest on the left to largest on the right (largest value on the scale in this case being about 5.5 kDa in size), this graphic shows a large majority of the peptides in the protein peptide product are less than 2 kDa which would relate to amino acid residues of 15-20 in length and shorter. By comparison the largest protein in the HDL would be almost 80-100 times that size. If the peptides have an ionic charge, it will bring the peak to the left and make it look smaller than it is. If the charge of the molecule is 1 then the scale on the bottom is equivalent to daltons. The y axis is a reflection of the amount of that exact mass/charge molecules exiting the separation column at the same time. A high peak means there is a spike of peptides with that exact mass/charge in the mixture exiting the column all at the same time. The general shape of the graph as a hill with spikes means that there is a large mixture of many different size peptides in the mixture (making up the hill) with the peaks meaning there are some common peptides which show up with higher frequency than others in the mixture. In this MALDI, the values approach zero by 3000 m/z. The graph does not get to zero below 500 m/z meaning there are peptides shorter than 500 which are not reflected on this MALDI.

In some embodiments, the method can be implemented using egg yolks as a starting point, rather than isolated granules. What is important in the process is disrupting the molecular bond between HDL and phosvitin. Controlled hydrolysis of the HDL with attached phosvitin, whether in liquid yolk or in the isolated granules, is what releases the phosvitin through the disruption of that bond. Once that bond is broken or disrupted the phosvitin is soluble and floats free in solution. A controlled proteolytic hydrolysis of the yolk will just as effectively disrupt those bonds as we have shown being done with just the granules portion, although with the variables in the hydrolysis modified appropriately.

Herein, the egg yolk composition comprises a combination of avian egg yolk phosvitin and HDL proteins. The egg yolk elements may be an egg yolk plasma, dried egg yolk unmodified egg yolk or other forms of egg yolks containing egg yolk phosvitin and HDL proteins. Preferably, the egg yolk elements are egg yolk elements from chicken eggs. The chicken may be a hen of any domesticated breed of chicken, since the egg yolks of hens of all domesticated breeds of chicken contain substantially similar proteins. Other avian eggs may also be used since they have a similar composition of plasma. The type of bird, diet and other factors may affect yolk quality and constituent parts as does egg yolk age. However, other avian egg yolks other than chicken may be of limited industrial applicability since other avian eggs are generally considerably more expensive than chicken eggs.

Immaterial modifications may be made to the embodiments described here without departing from what is covered by the claims.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A method of separating phosvitin and high-density lipoprotein (HDL) proteins from an egg yolk composition, the egg yolk composition including HDL proteins bound to phosvitin, the method comprising:
   selectively hydrolysing at least a portion of the HDL proteins using one or more proteolytic enzymes to cause the HDL proteins and phosvitin to become unbound and forming a hydrolysed solution comprising hydrolysed HDL, phosvitin and peptides, in which at least a portion of the phosvitin in the egg yolk composition is both: a) unbound from the HDL proteins, and b) remains fully unhydrolysed; and
   separating the hydrolysed HDL from the phosvitin and peptides to form a separated hydrolysed HDL composition and a separated phosvitin and peptide solution.

2. The method of claim 1, in which the egg yolk composition is undenatured prior to the step of hydrolysing the HDL proteins.

3. The method of claim 1, in which hydrolysing the HDL proteins using a proteolytic enzyme further comprises hydrolysing the HDL proteins using a combination of more than one proteolytic enzymes.

4. The method of claim 3, in which the combination of more than one proteolytic enzymes including at least pepsin and acid stable protease.

5. The method of claim 1, in which the egg yolk composition further comprises egg yolk granules and the method comprises
mixing water with the egg yolk granules;
reducing the pH of the water and egg yolk granules to form a reduced pH mixture;
adding pepsin to the reduced pH mixture;
mixing the reduced pH mixture and pepsin;
adding acid stable protease to the mixture of reduced pH mixture and pepsin;
mixing the reduced pH mixture, pepsin and acid stable protease; and
increasing the pH of the reduced pH mixture, pepsin and acid stable protease to form the hydrolysed solution.

6. The method of claim 5, in which reducing the pH of the water and egg yolk granules comprises adding hydrochloric acid.

7. The method of claim 5, in which increasing the pH to form the hydrolysed solution comprises adding sodium hydroxide.

8. The method of claim 5, comprising the step of obtaining the egg yolk granules from an egg yolk and in which obtaining the egg yolk granules comprises:
mixing water with egg yolk to form a mixed product including yolk plasma and granules, the yolk plasma including proteins and phospholipids; and
separating the yolk plasma and granules to form the egg yolk granules.

9. The method of claim 8, in which mixing water with egg yolk to form a mixed product comprises mixing water and salt with egg yolk to form the mixed product.

10. The method of claim 1, in which separating the unbound HDL proteins from the phosvitin further comprises:
diluting the hydrolysed solution with water to form a diluted hydrolysed solution; and
removing hydrolysed HDL from the diluted hydrolysed solution.

11. The method of claim 1, in which the separating the hydrolysed HDL further comprises centrifuging the hydrolysed solution to precipitate out the hydrolysed HDL and forming a supernatant solution of phosvitin and peptides.

12. The method of claim 11, further comprising filtering the supernatant solution to remove any remaining unhydrolyzed or substantially intact HDL protein or lipoproteins to form a phosvitin product with a higher concentration of phosvitin and peptides.

13. The method of claim 12, further comprising drying the phosvitin product.

14. The method of claim 1, further comprising drying the separated hydrolysed HDL composition to form a hydrolysed HDL product.

15. The method of claim 14, further comprising mixing the separated hydrolysed HDL composition into water and spray drying the mixture of water and separated hydrolysed HDL composition to form a hydrolysed HDL powder.

16. The method of claim 1, further comprising filtering the separated phosvitin and peptide solution to form a purified phosvitin product.

17. The method of claim 1 further comprising filtering the separated phosvitin and peptide solution to form a peptide product comprising a portion of phosvitin phosphopeptides and a portion of peptides from HDL.

18. The method of claim 1, in which hydrolysing at least a portion of the HDL proteins to cause the HDL proteins and phosvitin to become unbound and forming a hydrolysed solution comprising hydrolysed HDL, phosvitin and peptides further comprising hydrolysing all of the HDL proteins.

* * * * *